(12) United States Patent
Pilgaonkar et al.

(10) Patent No.: US 11,013,729 B2
(45) Date of Patent: May 25, 2021

(54) ORAL PHARMACEUTICAL COMPOSITIONS OF DABIGATRAN ETEXILATE

(71) Applicant: TOWA Pharmaceutical Europe, S.L. Unipersonal, Barcelona (ES)

(72) Inventors: Pratibha S. Pilgaonkar, Mumbai (IN); Maharukh T. Rustomjee, Mumbai (IN); Anilkumar S. Gandhi, Mumbai (IN)

(73) Assignee: TOWA Pharmaceutical Europe, S.L. Unipersonal, Barcelona (ES)

( * ) Notice: Subject to any disclaimer, the term of this patent is extended or adjusted under 35 U.S.C. 154(b) by 321 days.

(21) Appl. No.: 14/379,613

(22) PCT Filed: Feb. 21, 2013

(86) PCT No.: PCT/EP2013/053426
§ 371 (c)(1),
(2) Date: Aug. 19, 2014

(87) PCT Pub. No.: WO2013/124340
PCT Pub. Date: Aug. 29, 2013

(65) Prior Publication Data
US 2015/0030680 A1    Jan. 29, 2015

(30) Foreign Application Priority Data
Feb. 21, 2012   (IN) ............................ 461/MUM/2012

(51) Int. Cl.
| | | |
|---|---|---|
| A61K 31/4439 | (2006.01) | |
| A61K 9/16 | (2006.01) | |
| A61K 9/50 | (2006.01) | |
| A61K 9/14 | (2006.01) | |
| A61K 9/48 | (2006.01) | |

(52) U.S. Cl.
CPC ............ *A61K 31/4439* (2013.01); *A61K 9/14* (2013.01); *A61K 9/1617* (2013.01); *A61K 9/1652* (2013.01); *A61K 9/4833* (2013.01); *A61K 9/5026* (2013.01); *A61K 9/5042* (2013.01); *A61K 9/5084* (2013.01); *A61K 9/5089* (2013.01)

(58) Field of Classification Search
CPC .... A61K 31/4439; A61K 9/14; A61K 9/1617; A61K 9/1652; A61K 9/4833; A61K 9/5026; A61K 9/5042; A61K 9/5084; A61K 9/5089; A61P 7/02
See application file for complete search history.

(56) References Cited

U.S. PATENT DOCUMENTS

| | | | |
|---|---|---|---|
| 6,087,380 A | 7/2000 | Hauel et al. | |
| 2004/0109890 A1 | 6/2004 | Sugimoto | |
| 2005/0038077 A1 | 2/2005 | Kohlrausch | |
| 2005/0123606 A1 | 6/2005 | Kidane | |
| 2005/0234104 A1 | 10/2005 | Schmid et al. | |
| 2006/0074056 A1 | 4/2006 | Vaisburg et al. | |
| 2006/0183779 A1* | 8/2006 | Brauns ................ | C07D 401/12 514/338 |
| 2008/0069891 A1* | 3/2008 | Habib ................ | A61K 9/1652 424/494 |
| 2011/0129538 A1 | 6/2011 | Landerer et al. | |

FOREIGN PATENT DOCUMENTS

| | | |
|---|---|---|
| CA | 2476054 | 9/2003 |
| CN | 101632668 | 1/2010 |
| EP | 1366760 | 2/2002 |
| JP | H04103525 | 4/1992 |
| JP | 2001-524131 | 11/2001 |
| JP | 2002-523443 | 7/2002 |
| JP | 2002-316923 | 10/2002 |
| JP | 2005-519099 | 6/2005 |
| JP | 2007-510655 | 4/2007 |
| JP | 2008-501702 | 1/2008 |
| JP | 2008-534681 | 8/2008 |
| WO | WO 98/37075 | 8/1998 |
| WO | WO 98/50019 | 11/1998 |
| WO | WO 00/12064 | 3/2000 |
| WO | WO 03/074056 | 9/2003 |
| WO | WO 2005/028468 | 3/2005 |
| WO | WO 2005/046663 | 5/2005 |
| WO | WO 2005/121102 | 12/2005 |
| WO | WO 2007/092026 | 8/2007 |
| WO | WO 2012/001156 | 1/2012 |

OTHER PUBLICATIONS

Vippagunta et al. "Crystalline Solids," Advanced Drug Delivery Reviews, (2001), 48, pp. 3-26.*
Müller, Inorganic Chemistry, (1993) pp. 14-15.*
Wikipedia, Dabigatran, (Sep. 25, 2015), pp. 1-4.*
PubChem, Dabigatran Etexilate, (accessed Mar. 21, 2016), pp. 1-25.*
International Search Report for PCT/EP2013/053426 dated Apr. 16, 2013.
Belousov, Yu. B., et al., Rational Pharmacotherapy in Cardiology, vol. 8, No. 1, p. 37-44, 2012, English Abstract.
Bozhkova, S.A, Traumatology and Orthopedics, vol. 1, No. 59, p. 138-143, 2011, English Abstract.
Stangier, Clin Pharmacokinet 2008; 47 (5); 285-295.
Australian Public Assessment Report for Dabigatran Etexilate Mesylate, May 2011.
Declaration under 37 C.F.R. 1.132 of Dr. Ulrich Brauns filed in U.S. Appl. No. 11/381,890 dated Mar. 11, 2014.

* cited by examiner

Primary Examiner — Andrew S Rosenthal
Assistant Examiner — Lyndsey M Beckhardt
(74) Attorney, Agent, or Firm — Melissa M. Hayworth; E. Joseph Gess; Daniel R. Evans

(57) ABSTRACT

Compositions comprising a mixture of at least two types of particles wherein a) the first type of particles comprise dabigatran etexilate in the form of the free base or in the form of pharmaceutically acceptable salts, polymorphs, solvates or hydrates thereof; and b) the second type of particles comprise at least one pharmaceutically acceptable organic acid, use of said compositions in the reduction of the risk of stroke and systemic embolism in patients with non-valvular atrial fibrillation and/or in the prevention of venous thromboembolic events in adult patients who have undergone elective total hip replacement surgery or total knee replacement surgery and processes for the preparation of said compositions.

18 Claims, No Drawings

ORAL PHARMACEUTICAL COMPOSITIONS OF DABIGATRAN ETEXILATE

FIELD OF INVENTION

The present invention relates to oral pharmaceutical compositions comprising dabigatran etexilate or pharmaceutically acceptable salts thereof.

BACKGROUND OF THE INVENTION

Atrial fibrillation is the most common cardiac arrhythmia which is characterized by abnormal heart rhythm. It is considered to be a common cause of irregular heart beat and can cause stroke and other systemic embolic events, eventually leading to death.

It has been seen that the incidence of atrial fibrillation increases with age and nearly 6% of individuals over the age of 65 are affected while the prevalence is about 8% in individuals over the age of 80. The lack of organized cardiac contractions in atrial fibrillation generally results in some stagnant blood in the left atrium or left atrial appendage. This lack of movement of blood leads to thrombus formation or blood clotting. Patients with atrial fibrillation are therefore at greater risk of developing clots which increases the risk of stroke and other systemic embolic events. Since the consequence of stroke or systemic embolism is devastating, a primary aim of therapy for atrial fibrillation is to reduce the risk of arterial thrombus formation and thromboembolism. Anticoagulants such as warfarin are mainly used in case of atrial fibrillation along with other medications such as beta blockers and calcium channel blockers or some noninvasive rhythm control methods. Though anticoagulation therapy with warfarin has been shown to significantly reduce the incidence of stroke or systemic embolism, its use is found to be cumbersome due to multiple diet and drug interactions, chances of hemorrhage which are difficult to manage, requirement of frequent laboratory monitoring etc. Use of a newer safe and effective anticoagulant is therefore necessary.

Direct thrombin inhibitors, is another class of anticoagulants that act by directly inhibiting the enzyme thrombin and are expected to replace heparin (and derivatives) and warfarin in various clinical scenarios. Thrombin, a serine protease protein formed by proteolytic cleavage of prothrombin, converts soluble fibrinogen into insoluble strands of fibrin and further catalyzes many other coagulation-related reactions. Direct thrombin inhibitors inhibit thrombin including fibrin-bound thrombin, thereby delimiting thrombus growth, provide predictable anticoagulant responses because they are not bound to plasma proteins and have no drug-drug interactions. Depending on their interaction with the thrombin molecule, there are bivalent as well as univalent types of direct thrombin inhibitors, with some being in clinical use, while others undergoing clinical development.

Dabigatran is a potent, reversible, univalent direct thrombin inhibitor. It reduces the risk of stroke and systemic embolism in patients with non-valvular atrial fibrillation. It is also useful in primary prevention of venous thromboembolic events in adult patients who have undergone elective total hip replacement surgery or total knee replacement surgery. Dabigatran inhibits free thrombin, fibrin-bound thrombin and thrombin-induced platelet aggregation. Dabigatran was first disclosed in WO98/37075, which claimed compounds with a thrombin-inhibiting effect and the effect of prolonging the thrombin time, under the name 1-methyl-2-[N-[4-(N-n-hexyloxycarbonylamidino) phenyl]aminomethyl]benzimidazol-5-ylcarboxylic acid-N-(2-pyridyl)-N-(2 ethoxycarbonylethyl)amides.

Dabigatran is currently available as dabigatran etexilate mesylate (DEM) under the brand name Pradaxa® from Boehringer Ingelheim as immediate release oral capsules of 75 mg and 110 mg (in Europe) and 75 mg and 150 mg strengths (in the United States) to be administered twice daily. DEM is a salt form of the prodrug dabigatran etexilate which after oral administration is absorbed and converted to dabigatran by esterase-catalysed hydrolysis in the liver. DEM is a yellow-white to yellow non-hygroscopic powder that exists in two anhydrous polymorphic forms, Form I and II, which are described in WO 2005/028468. The aqueous solubility of DEM is strongly pH dependent with rather high solubility in acidic media and very poor solubility in neutral and basic media while solubility in water is 1.8 mg/mL. The absolute bioavailability of dabigatran following oral administration of dabigatran etexilate is approximately about 3-7% and elimination half life is 12-17 hours. DEM is BCS Class II drug, indicating poor aqueous solubility but good membrane permeability. DEM is stable in the solid state and not sensitive to light irradiation but it predominantly undergoes degradation by hydrolytic pathways in the presence of moisture. It is also acid sensitive.

Due to these physicochemical and biopharmaceutical properties of DEM, some attempts have been made to provide compositions of DEM that are stable and/or provide desirable in vitro release and bioavailability.

U.S. Patent Application 2006/0183779A1 describes pharmaceutical compositions of DEM for oral administration in the form of pellets comprising (a) substantially spherical core material comprised of one or more pharmaceutically acceptable organic acids with a water solubility of >1 g/250 ml at 20° C. such as tartaric acid; and (b) an active substance layer containing one or more binders and optionally a separating agent, that encloses said core material. The separating agent layer or insulating layer separates the acid core from the active substance containing layer. The layer of active substance may in turn be enclosed in a coating which increases the abrasion resistance and shelf life of the pellets. Such layered pellets are later filled into hard capsules. However, the process of preparing layered pellets is cumbersome, time consuming and uneconomical.

U.S. Patent Application 2005/0038077 discloses a tablet comprising dabigatran etexilate or pharmaceutically acceptable salt thereof; one or more pharmaceutically acceptable organic acids with a solubility in water of >1 g/250 ml at 20° C. and a pharmaceutically acceptable excipient or filler. However due to the presence of an organic acid in close contact with the active in a tablet composition without any special steps taken to separate the two from each other, can make the active highly susceptible to hydrolysis in the presence of humidity.

The above attempts only provided compositions of DEM, which are either tedious or technologically demanding to prepare or are unlikely to remain stable over the shelf life of the product. Need therefore exists to prepare alternate compositions of dabigatran etexilate that are stable, easy or convenient to prepare, provide the desired in vitro release and bioavailability.

The present inventors after rigorous experimentation provide oral compositions of dabigatran etexilate comprising a mixture of at least two types of particles and optionally at least one pharmaceutically acceptable excipient, wherein a) the first type of particles comprise the active agent; b) the second type of particles comprise at least one pharmaceutically acceptable organic acid; and c) optionally at least one type of particles are coated with a protective coating layer. Such compositions are chemically and polymorphically stable, provide desired in-vitro and in-vivo performance and can be prepared by simple, non-tedious and cost-effective process. In particular, the compositions of the present invention provide a quick dissolution particularly at earlier time points as compared to formulation having one type of particles/pellets. Such a faster dissolution at earlier time points can ensure availability of more amount of active especially when (a) absorption of the active is rapid with faster Tmax (~45 minutes-1 hour), (b) significant bioactivation is involved and (c) negligible and variable absorption at higher pH.

DETAILED DESCRIPTION OF THE INVENTION

The present invention provides, in one of its aspects, pharmaceutical compositions, preferably for oral administration, comprising a mixture of at least two types of particles and optionally at least one pharmaceutically acceptable excipient, wherein a) the first type of particles comprise dabigatran etexilate in the form of the free base or in the form of pharmaceutically acceptable salts, polymorphs, solvates or hydrates thereof; and b) the second type of particles comprise at least one pharmaceutically acceptable organic acid.

In a particular embodiment, the present invention provides pharmaceutical compositions, preferably for oral administration, comprising a mixture of at least two types of particles and optionally at least one pharmaceutically acceptable excipient, wherein a) the first type of particles comprise dabigatran etexilate in the form of free base or in the form of pharmaceutically acceptable salts, polymorphs, solvates or hydrates thereof; b) the second type of particles comprise at least one pharmaceutically acceptable organic acid; and c) optionally at least one type of particles are coated with a protective coating layer.

The compositions of the present invention are stable, easy to prepare, and provide the desired in-vitro release of the active.

The first type of particles present in the composition of the present invention, comprise dabigatran etexilate. Dabigatran etexilate may be used in the compositions of the present invention as the free base (3-[(2-{4-(hexyloxycarbonylamino-imino-methyl)-phenylamino]methyl}-1-methyl-1H-benzimidazol-5-carbonyl)-pyridin-2-yl-amino-propionic acid ethyl ester) or in the form of pharmaceutically acceptable salts, polymorphs, solvates, hydrates thereof. For the sake of conciseness, the term dabigatran etexilate is employed in this specification to designate any of the above-mentioned forms except when the term is further qualified (i.e. dabigatran etexilate mesylate). Whenever it is necessary to designate the free base of dabigatran etexilate the term "dabigatran etexilate (free base)" is employed.

The term "pharmaceutically acceptable salt" refers to those salts which are, according to medical judgement, suitable for use in contact with the tissues of humans and other mammals without undue toxicity, irritation, allergic response and the like. Pharmaceutically acceptable salts are well known in the art.

In one embodiment the amount of dabigatran etexilate (expressed as dabigatran etexilate mesylate) in the composition can vary from about 0.01 weight % to about 90 weight %, based on the total weight of the composition. In another embodiment the amount of dabigatran etexilate in the composition can vary from about 0.02 weight % to about 85 weight %, based on the total weight of the composition. In still another embodiment, the amount of dabigatran etexilate in the composition can vary from about 0.05 weight % to about 80 weight %, based on the total weight of the composition.

In one embodiment the compositions of the present invention may be in the form of unit dose forms comprising from 50 mg to 200 mg of dabigatran etexilate mesylate, preferably from 75 mg to 150 mg, more preferably 75 mg, 110 mg or 150 mg.

In one embodiment of the present invention dabigatran etexilate is used in the form of the mesylate salt, i.e. dabigatran etexilate mesylate.

In a particular embodiment of the present invention dabigatran etexilate is used in the form of polymorphic form I of dabigatran etexilate mesylate (as described in WO 2005/028468).

In another particular embodiment of the present invention dabigatran etexilate is used in the form of polymorphic form II of dabigatran etexilate mesylate (as described in WO 2005/028468).

The oral pharmaceutical composition of the present invention comprises a mixture of at least two types of particles and optionally at least one pharmaceutically acceptable excipient, with a first type of particles comprising dabigatran etexilate and second type of particles comprising at least one pharmaceutically acceptable organic acid.

In a preferred embodiment of the present invention the first type of particles comprising dabigatran etexilate is free from organic and inorganic acids.

In a preferred embodiment of the present invention the first type of particles comprising dabigatran etexilate in the form of the free base or in the form of pharmaceutically acceptable salts, polymorphs, solvates or hydrates thereof also comprise at least one pharmaceutical excipient.

In a most preferred embodiment of the present invention, the said first type of particles comprising dabigatran etexilate mesylate in the form of the free base or in the form of pharmaceutically acceptable salts, polymorphs, solvates or hydrates thereof also comprise one or more excipients selected from the group consisting of binders, diluents and/or lubricants.

In a particular embodiment said first type of particles comprise at least one binder, preferably microcrystalline cellulose.

In another particular embodiment, said first type of particles comprises at least one disintegrant, preferably selected from sodium croscarmellose or crospovidone.

In another particular embodiment, said first type of particles comprise at least one diluent, preferably selected from mannitol or lactose.

In another particular embodiment, said first type of particles comprise at least one binder, preferably microcrystalline cellulose, a disintegrant, preferably selected from sodium croscarmellose or crospovidone and a diluent, preferably selected from mannitol or lactose.

In another preferred embodiment of the present invention the second type of particles comprising at least one pharmaceutically acceptable organic acid is free from dabigatran etexilate.

In a most preferred embodiment of the present invention the first type of particles comprising dabigatran etexilate is free from acids and the second type of particles comprising at least one pharmaceutically acceptable organic acid is free from dabigatran etexilate.

In another preferred embodiment of the present invention the second type of particles comprise tartaric acid, preferably in the form of pellets with a particle size between 100 and 900 microns, more preferably between 400 and 700 microns.

An acid is a substance that releases hydrogen ions and decreases the pH of an aqueous solution.

Organic acids that may be employed in the present composition include, but are not limited to, tartaric acid, fumaric acid, succinic acid, citric acid, malic acid, glutamic acid, aspartic acid and the like or combinations thereof including the hydrates and acid salts thereof.

In one embodiment the organic acid is present in the composition of the present invention in an amount of about 2% by weight to about 95% by weight of the composition. In another embodiment the organic acid is present in the composition of the present invention in an amount of about 5% by weight to about 90% by weight of the composition. In a further embodiment the organic acid is present in the composition of the present invention in an amount of about 10% by weight to about 85% by weight of the composition.

In one embodiment at least 90% by weight, preferably at least 95% by weight, more preferably at least 99% by weight and still more preferably 100% by weight of the organic acid present in the composition is contained in the second type of particles which comprise at least one pharmaceutically acceptable organic acid, the rest (if any) of the organic acid being added as part of the excipients.

Further the oral pharmaceutical compositions of the present invention comprise a mixture of at least two types of particles and optionally at least one pharmaceutically acceptable excipient, wherein optionally at least one type of particles are coated with a protective coating layer. In one embodiment, the first type of particles is coated with a protective coating layer. In another embodiment, the second type of particles is coated with a protective coating layer. In yet another embodiment, the first and the second type of particles are coated with a protective coating layer.

The term "protective coating layer" as used herein is intended to mean a layer of a polymeric or a non-polymeric material disposed on the surface of a particle core in order to avoid direct contact of the particle core with its environment.

In one embodiment, protective coating layer is formed of a polymeric or a non-polymeric pharmaceutically acceptable agent or any combination thereof.

The polymeric pharmaceutically acceptable agents used for the protective coating layer include, but are not limited to, cellulose derivatives, vinyl derivatives, polymers and copolymers, gums, acrylic or methacrylic acid polymers, copolymers, esters or derivatives thereof, and the like or combinations thereof. Cellulose derivatives that may be employed, include, but are not limited to, methylcellulose, hydroxypropylmethylcellulose, hydroxypropyl cellulose, hydroxyethyl cellulose, hydroxymethyl cellulose, ethylcellulose, hydroxypropyl ethylcellulose, carboxymethylethyl cellulose, carboxy ethylcellulose, carboxymethyl hydroxyethylcellulose, hydroxyethylmethyl carboxymethyl cellulose, hydroxyethyl methyl cellulose, carboxymethyl cellulose, methylhydroxyethyl cellulose, methylhydroxypropyl cellulose, carboxymethyl sulfoethyl cellulose, sodium carboxymethyl cellulose, and the like or combinations thereof. Vinyl derivatives, polymers and copolymers thereof that may be employed include, but are not limited to copolymers of vinyl pyrrolidone, copolymers of polyvinyl alcohol (Kollicoat IR), polyvinylpyrrolidone or combinations thereof. Gums that may be employed include, but are not limited to, gum arabic, alginates, guar gum, locust bean gum, carrageenan, pectin, xanthan gum, gellan gum, maltodextrin, galactomannan, karaya, and the like, or combinations. Acrylic or methacrylic acid polymers, copolymers, esters or derivatives thereof, that may be employed include, but are not limited to, a) copolymer formed from monomers selected from methacrylic acid, methacrylic acid esters, acrylic acid and acrylic acid esters b) copolymer formed from monomers selected from butyl methacrylate, (2-dimethylaminoethyl)methacrylate and methyl methacrylate c) copolymer formed from monomers selected from ethyl acrylate, methyl methacrylate and trimethylammonioethyl methacrylate chloride or d) copolymers of acrylate and methacrylates with/without quarternary ammonium group in combination with sodium carboxymethylcellulose, e.g. those available from Röhm GmbH under the trademark Eudragit® like Eudragit EPO (dimethylaminoethyl methacrylate copolymer; basic butylated methacrylate copolymer), Eudragit RL and RS (trimethylammonioethyl methacrylate copolymer), Eudragit NE30D and Eudragit NE40D (ethylacrylate methymethacrylate copolymer), Eudragit RD 100 (ammoniomethacrylate copolymer with sodium carboxymethylcellulose); or the like or any combinations thereof.

The non-polymeric pharmaceutically acceptable agents used for the protective coating layer include, but are not limited to C8-C22 fatty acids, C8-C22 fatty alcohols, fats, in particular mono-, di- or triesters of glycerol and C8-C22 fatty acids, waxes, and the like, or combinations thereof. Fatty acids that may be employed include, but are not limited to, decenoic acid, docosanoic acid, stearic acid, palmitic acid, lauric acid, myristic acid, hydrogenated palm kernel oil, hydrogenated peanut oil, hydrogenated palm oil, hydrogenated rapeseed oil, hydrogenated rice bran oil, hydrogenated soybean oil, hydrogenated sunflower oil, hydrogenated castor oil, hydrogenated cottonseed oil, and the like, and mixtures thereof. Long chain monohydric alcohols that may be employed include, but are not limited to, cetyl alcohol, stearyl alcohol and mixtures thereof. Waxes that may be employed include, but are not limited to, spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, carbowax, glyceryl monostearate, glyceryl distearate, glyceryl tristearate, glyceryl dipalmitate, glyceryl tripalmitate, glyceryl monopalmitate, glyceryl dilaurate, glyceryl trilaurate, glyceryl monolaurate, glyceryl trimyristate, glyceryl monodecenoate, glyceryl didecenoate, glyceryl tridecenoate, glyceryl behenate and the like, or mixtures thereof.

In a further embodiment, in addition to polymeric or non-polymeric pharmaceutically acceptable agent or any combination thereof, the protective coating layer may optionally further comprise one or more pharmaceutically acceptable excipients such as, but not limited to, plasticizer, anti-tacking agent, pigment, and the like, or combinations thereof. A plasticizer that may be employed includes, but is not limited to, triethyl citrate, acetyl triethyl citrate, propylene glycol, polyethylene glycol, acetyl tributyl citrate, acetylated monoglycerides, glycerin, triacetin, phthalate esters (e.g., diethyl phthalate, dibutyl phthalate), castor oil, sorbitol and dibutyl seccate or a combination thereof. An anti-tacking agent that may be employed includes, but is not limited to, talc, or glyceryl monostearate. A pigment such as, but not limited to, titanium dioxide, iron oxide, or a mixture thereof may be employed.

The protective coating layer may be optionally applied onto at least one type of particles of the present invention. For example, the protective coating layer is applied onto the first type of particles which comprise dabigatran etexilate in the form of free base or in the form of pharmaceutically acceptable salts, polymorphs, solvates or hydrates thereof.

In a preferred embodiment of the present invention the protective coating layer is coated onto the second type of particles which comprise at least one pharmaceutically acceptable organic acid. In a particular embodiment said coating layer comprises hydroxypropylmethyl cellulose and talc.

In another embodiment, both particles are coated with the said protective coating layer.

The protective coating layer may be optionally applied onto at least a type of particles of the present invention in any suitable equipment where coating can be achieved, such as, but not limited to, coating pan, conventional film coating apparatus or a fluidized bed apparatus, or the like. Furthermore, in one embodiment, the protective coating layer can be applied from an aqueous or organic solution or dispersion. In another embodiment, the particles being coated with the protective coating layer may be coated to a weight gain of about 2% to about 50% by weight.

In one embodiment, in order to reduce any damage to the protective coating layer during transfer into capsules, the particles coated with the protective coating layer may be further seal coated with conventional pharmaceutically acceptable film forming agents which may optionally be combined with plasticizers or pigments. Suitable film forming agents include, but are not limited to, hydroxypropyl cellulose, hydroxypropyl methylcellulose, acrylic and methacrylic acid polymers, copolymers or esters, and the like or combinations thereof. Plasticizers or pigments as discussed above may optionally be used with the film forming agents.

The compositions of the present invention comprise a mixture of at least two types of particles and optionally at least one pharmaceutically acceptable excipient. In a further embodiment, the first type of particles comprising dabigatran etexilate may optionally further comprise at least one pharmaceutically acceptable excipient. In another embodiment, the second type of particles comprising at least one organic acid, may optionally further comprise at least one pharmaceutically acceptable excipient. In yet another embodiment, at least two types of particles that are present in the pharmaceutical composition optionally further comprise at least one pharmaceutically acceptable excipient.

The pharmaceutically acceptable excipients that may be incorporated in the composition of the present invention include, but are not limited to, binders, disintegrants, diluents, surfactants, glidants, lubricants, and the like or combinations thereof.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, natural, modified or pregelatinized starch, modified starches (such as sodium starch glycolate) and partially pregelatinized starches (such as Starch 1500), polyvinylpyrrolidone, crospovidone, croscarmellose sodium, calcium silicate clays, such as bentonite, microcrystalline cellulose, gums such as agar, guar, locust bean, karaya, pectin, tragacanth, alginates, ion exange resins (such as Polacrilin potassium, Polacrilex) Neusilins, low substituted hydroxypropyl cellulose and the like, combinations thereof and other such materials known to those of ordinary skill in the art.

The term "binders" as used herein is intended to mean substances used to cause adhesion of powder particles in granulations. Examples of suitable binders include, but are not limited to celluloses such as microcrystalline cellulose, modified celluloses (such as low substituted hydroxypropyl cellulose, hydroxypropyl cellulose (or HPC), hydroxypropyl methylcellulose (or HPMC or hypromellose), hydroxyethylcellulose, hydroxyethyl methylcellulose, ethyl cellulose, cellulose gum, xanthan gum, sugars (such as sucrose, glucose, amilose, maltodextrin, dextrose and the like), starches such as corn or potato starch partially pregelatinized starches (such as Starch 1500), polyvinyl acetate (Kollicoat SR), polyvinyl alcohol-polyethylene glycol graft copolymer (Kollicoat IR), copovidone, cross-linked polyvinylpyrrolidone, acrylic acid polymer (Carbopol), poloxamer, polycarbophil, polyethylene oxide, polyethylene glycol, and the like, combinations thereof and other material known to those of ordinary skill in the art.

The term "diluent" or "filler" as used herein is intended to mean inert substances used as fillers to create the desired bulk, flow properties, and compression characteristics in the preparation of solid dosage formulations. Examples of suitable diluents include, but are not limited to microcrystalline cellulose, coprocessed microcrystalline celluloses (such as Avicel CI-611, Avicel RC-581, Avicel RC591, Avicel CE, Avicel DG, Avicel HFE), lactose, sucrose, xylitol, mannitol, maltose, polyols, fructose, guar gum, sorbitol, magnesium hydroxide, dibasic calcium phosphate, kaolin, calcium sulphate, carrageenan, chitosan, pectinic acid, sodium alginate, magnesium aluminium silicate, calcium carbonate and the like, combinations thereof and other such materials known to those of ordinary skill in the art.

The term "lubricant" as used herein is intended to mean substances used in solid dosage formulations to reduce friction during compression of the solid dosage. Such compounds include, but are not limited to, magnesium stearate, calcium stearate, zinc stearate, stearic acid, talc, mineral oil and sodium stearyl fumarate, combinations thereof and other such materials known to those of ordinary skill in the art.

The tablet compositions of the invention may also include a glidant. The term "glidant" as used herein is intended to mean agents used in solid dosage formulations to improve flow-properties during tablet compression and to produce an anti-caking effect. Such compounds include, but not limited to, colloidal silica, silica gel, precipitated silica, calcium silicate, magnesium silicate, cornstarch, talc, combinations thereof and other such materials known to those of ordinary skill in the art.

The term "surfactant" as used herein is intended to mean substances used to reduce the surface tension of the aqueous solutions comprising them. Examples of surfactants include, but are not limited to, sodium docusate, glyceryl monooleate, polyethylene alkyl ether, polyoxyethylene sorbitan fatty acid ester, sodium lauryl sulfate, sorbic acid, sorbitan fatty acid ester, mixtures thereof and other such materials known to those of ordinary skill in the art.

The compositions of the present invention comprise a mixture of at least two types of particles and optionally at least one pharmaceutically acceptable excipient, with first type of particles comprising dabigatran etexilate and second type of particles comprising at least one organic acid.

The term "particle" as used herein is intended to mean any solid or semi-solid portion of a substance or a composition having defined physical boundaries. Examples of particles include, but are not limited to, powder, granules, pellets, beads, minitablets or the like. The granules may be prepared by methods such as, but not limited to, wet granulation, melt granulation, dry granulation or roll compaction or the like. In an embodiment of the present invention, pellets may be prepared using extrusion spheronization. In another embodiment of the present invention, dabigatran etexilate present in the first set of particles or at least one organic acid present in the second set of particles can be loaded on an inert carrier. The inert carrier can be selected from, but not limited to, beads, pellets, spheres or similar particles that do not contain an active ingredient. Non-limiting examples of inert carrier include microcrystalline cellulose, sugar or silicon dioxide. In yet another embodiment, the particles of the present invention, in the powder form, may be incorporated in the compositions of the present invention.

In an embodiment of the present invention said first type of particles has a particle size comprised between 50 and 1000 microns and said second type of particles have a particle size comprised between 100 and 1000 microns.

The compositions of the present invention comprise from about 5% to about 100% by weight of the mixture of at least two types of particles. Ratio of the first and second types of particles is from about 1:99 to about 99:1.

The term "composition" or "formulation" has been employed interchangeably for the purpose of the present invention.

The term "dosage form" is as used herein is intended to mean a pharmaceutical composition which is suitable for administration to a patient. In one embodiment the compositions of the present invention can be in the form of capsules, tablets, minitablets, stick formulation, dispersible tablets, dry suspension for reconstitution, powder or granule for solution or suspension, granules, and the like or any combinations thereof. Depending of the final dosage form the compositions of the present invention may comprise appropriate pharmaceutically acceptable excipients such as those mentioned above or some additional ones such as, but not limited to, sweeteners, flavors, colorants and the like or combinations thereof. Further it is contemplated within the scope of the invention that the dosage form can be encapsulated or coated. In one embodiment, the composition of the present invention is in the form of a capsule. Capsules include, for example, hard capsules of gelatine or hydroxypropylmethylcellulose and the like. In a further embodiment, the compositions of the present invention may be manufactured using conventional techniques known in the art.

The term "unit dosage form" refers to a physically discrete unit suitable as a unitary dosage for a human patient such as a capsule, a tablet or a vial. In another aspect the present invention provides a unit dosage form prepared from the above mentioned compositions comprising two types of particles.

The compositions of the present invention provide flexibility of blending at least two types of particles to attain different release patterns. In one embodiment, the compositions of the present invention provide tailored in-vitro profiles and corresponding in-vivo profiles. In a further embodiment, the compositions of the present invention can provide tailored profiles wherein dissolution of the compositions of the present invention can be faster at initial time points when compared to formulations having only single type of particles comprising both dabigatran etexilate or pharmaceutically acceptable salts thereof and organic acid. Without being bound to any theory it is believed that such a faster dissolution at earlier time points can ensure availability of more amount of active especially when (a) absorption of the active is rapid with faster Tmax (~45 minutes-1 hour), (b) significant bioactivation is involved for action of dabigatran and (c) negligible and variable absorption is observed at higher pH.

In another aspect the present invention provides a process for the preparation of a composition comprising the two types of particles described above comprising the step of mixing said first type of particles and said second type of particles with a at least one pharmaceutically acceptable excipient. In a particular embodiment of the present invention said first type of particles are prepared by granulation.

In one embodiment the process of preparing the compositions of the present invention comprises the steps of
(i) blending dabigatran etexilate and at least one pharmaceutically acceptable excipient such as diluent;
(ii) granulating the blend of step (i) with a binder solution to form granules of the active agent;
(iii) blending at least one organic acid and at least one pharmaceutically acceptable excipient such as diluent;
(iv) granulating the blend of step (iii) with a binder solution to form organic acid granules;
(v) coating the organic acid granules with a protective coating layer;
(vi) blending the granules of step (ii) with the coated granules of step (v) to form a mixture of at least two types of granules;
(vii) optionally blending the mixture of at least two types of granules of step (vi) with at least one pharmaceutically acceptable excipient;
(viii) lubricating the blend of step (vii);
(ix) filling the lubricated mixture of step (viii) into suitable hard capsules.

In another embodiment the process of preparing the compositions of the present invention comprises the steps of
(i) blending dabigatran etexilate and at least one pharmaceutically acceptable excipient such as diluent;
(ii) granulating the blend of step (i) with a binder solution to form granules of the active agent;
(iii) blending at least one organic acid and at least one pharmaceutically acceptable excipient such as diluent;
(iv) granulating the blend of step (iii) with a binder solution to form organic acid granules;
(v) coating the granules of active agent with a protective coating layer;
(vi) blending the granules of step (iv) with the coated granules of step (v) to form a mixture of at least two types of granules;
(vii) optionally blending the mixture of at least two types of granules of step (vi) with at least one pharmaceutically acceptable excipient;
(viii) lubricating the blend of step (vii);
(ix) filling the lubricated mixture of step (viii) into suitable hard capsules.

In yet another embodiment the process of preparing the compositions of the present invention comprises the steps of
(i) blending dabigatran etexilate and at least one pharmaceutically acceptable excipient such as diluent;
(ii) granulating the blend of step (i) with a binder solution to form granules of the active agent;
(iii) blending at least one organic acid and at least one pharmaceutically acceptable excipient such as diluent or binder;
(iv) extruding and spheronizing the blend of step (iii) to form organic acid pellets;
(v) coating the organic acid pellets of step (iv) with a protective coating layer;
(vi) blending the granules of step (ii) with the coated pellets of step (v) to form a mixture of at least two types of particles;
(vii) optionally blending the mixture of at least two types of granules of step (vi) with at least one pharmaceutically acceptable excipient;

(viii) lubricating the blend of step (vii);
(ix) filling the lubricated mixture of step (viii) into suitable hard capsules.

In a further aspect the present invention provides the use of the pharmaceutical composition of dabigatran etexilate of the present invention for the manufacture of a medicament for reducing the risk of stroke and systemic embolism in patients with non-valvular atrial fibrillation and/or preventing venous thromboembolic events in adult patients who have undergone elective total hip replacement surgery or total knee replacement surgery.

In still another aspect the present invention provides a method of for reducing the risk of stroke and systemic embolism in patients with non-valvular atrial fibrillation and/or preventing venous thromboembolic events in adult patients who have undergone elective total hip replacement surgery or total knee replacement surgery, comprising administering to the subject in need thereof pharmaceutical compositions of dabigatran etexilate of the present invention.

In another embodiment of the present invention the dabigatran etexilate may be combined with other active agents or pharmaceutically acceptable salts thereof including, but not limited to, atorvastatin, dipyridamole, mopidamole and the like or combinations thereof.

The invention is further illustrated by the following examples, which are for illustrative purposes and should not be construed as limiting the scope of the invention in any way.

EXAMPLES

Example 1

Oral Capsule Formulation of Dabigatran Etexilate Mesylate

A) Preparation of Coated Tartaric Acid Pellets
  (a) Preparation of Tartaric Acid Pellets

TABLE 1

| Composition of tartaric acid pellets | |
| --- | --- |
| Ingredients | mg/unit |
| Tartaric acid | 80 |
| Microcrystalline cellulose | 30 |
| Hydroxypropyl cellulose | 10 |
| Isopropyl alcohol* | q.s |
| Total | 120 |

*not present in the final product

Procedure: Tartaric acid and microcrystalline cellulose were blended and to this blend was added solution of hydroxypropyl cellulose in isopropyl alcohol to get a wet mass. This wet mass was extruded, spheronized, dried and screened to give pellets. These pellets were then coated with a protective coating layer as follows to give coated tartaric acid pellets.
  (b) Preparation of Coated Tartaric Acid Pellets

TABLE 2

| Composition of tartaric acid pellets | |
| --- | --- |
| Ingredients | mg/unit |
| Tartaric acid pellets | 120 |
| Hydroxypropyl methylcellulose | 10 |

TABLE 2-continued

| Composition of tartaric acid pellets | |
| --- | --- |
| Ingredients | mg/unit |
| Talc | 6 |
| Isopropyl alcohol* | q.s |
| Total | 136 |

*not present in the final product

Procedure: Tartaric acid pellets prepared as above were coated with dispersion of hydroxypropyl cellulose and talc in isopropyl alcohol. The coated pellets were then dried to give coated tartaric acid pellets.

B) Preparation of Dabigatran Etexilate Mesylate Granules

TABLE 3

| Composition of dabigatran etexilate mesylate granules | |
| --- | --- |
| Ingredients | mg/unit |
| Dabigatran etexilate mesylate equivalent to 110 mg of dabigatran etexilate | 126.83 |
| Microcrystalline cellulose | 40.17 |
| Lactose anhydrous | 30 |
| Crospovidone | 4 |
| Hydroxypropyl cellulose | 4 |
| Isopropyl alcohol* | q.s |
| Total | 205 |

*not present in the final product

Procedure: Dabigatran etexilate mesylate, microcrystalline cellulose, lactose anhydrous and crospovidone were blended. The blend was granulated using solution of hydroxypropyl cellulose in isopropyl alcohol. The granules were sized and screened to form dabigatran etexilate mesylate granules.

C) Preparation of Oral Capsule Formulation of Dabigatran Etexilate Mesylate

TABLE 4

| Composition of capsule formulation of dabigatran etexilate mesylate | |
| --- | --- |
| Ingredients | mg/unit |
| Dabigatran etexilate mesylate granules | 205 |
| Coated tartaric acid pellets | 136 |
| Sodium stearyl fumarate | 4 |
| Total | 345 |

Procedure: Dabigatran etexilate mesylate granules prepared as per composition of Table 3 above and coated tartaric acid pellets prepared as per Table 2 above were blended. Blend was lubricated with sodium stearyl fumarate and filled into capsules by means of a capsule filling machine.

Example 2

Oral Capsule Formulation of Dabigatran Etexilate Mesylate

A) Preparation of Tartaric Acid Pellets

TABLE 5

Composition of tartaric acid pellets

| Ingredients | mg/unit |
|---|---|
| Tartaric acid | 60 |
| Microcrystalline cellulose | 18 |
| Hydroxypropyl cellulose | 4 |
| Isopropyl alcohol* | q.s |
| Total | 82 |

*not present in the final product

Procedure: Tartaric acid and microcrystalline cellulose were blended and to this blend was added solution of hydroxypropyl cellulose in isopropyl alcohol to get a wet mass. This wet mass was extruded, spheronized, dried and screened to give pellets. These pellets were then coated using with a protective coating layer as follows to give coated tartaric acid pellets.

B) Preparation of Dabigatran Etexilate Mesylate Coated Granules (a) Preparation of Dabigatran Etexilate Mesylate Granules

TABLE 6

Composition of dabigatran etexilate mesylate granules

| Ingredients | mg/unit |
|---|---|
| Dabigatran etexilate mesylate equivalent to 110 mg of dabigatran etexilate | 86.48 |
| Microcrystalline cellulose | 32.52 |
| Lactose anhydrous | 25 |
| Crospovidone | 3 |
| Hydroxypropyl cellulose | 3 |
| Isopropyl alcohol* | q.s |
| Total | 150 |

*not present in the final product

Procedure: Dabigatran etexilate mesylate, microcrystalline cellulose, lactose anhydrous and crospovidone were blended. The blend was granulated using solution of hydroxypropyl cellulose in isopropyl alcohol. The granules were sized and screened to form dabigatran etexilate mesylate granules.

(b) Preparation of Dabigatran Etexilate Mesylate Coated Granules

TABLE 7

Composition of dabigatran etexilate mesylate coated granules

| Ingredients | mg/unit |
|---|---|
| Dabigatran etexilate mesylate granules | 150 |
| Polyvinyl pyrrolidone | 22 |
| Talc | 3 |
| Isopropyl alcohol | q.s. |
| Total | 175 |

*not present in the final product

Procedure: Dabigatran etexilate mesylate granules prepared as per the process mentioned above were coated with a coating dispersion of polyvinyl pyrrolidone and talc in isopropyl alcohol to form coated dabigatran etexilate mesylate granules.

C) Preparation of Oral Capsule Formulation of Dabigatran Etexilate Mesylate

TABLE 8

Composition of capsule formulation of dabigatran etexilatemesylate

| Ingredients | mg/unit |
|---|---|
| Coated dabigatran etexilate mesylate granules | 175 |
| Tartaric acid pellets | 82 |
| Sodium stearyl fumarate | 3 |
| Total | 260 |

Procedure: Dabigatran etexilate mesylate granules prepared as per Table 7 above and coated tartaric acid pellets prepared as per table 5 above were blended. Blend was lubricated with sodium stearyl fumarate and filled into capsules by means of a capsule filling machine.

Example 3

Comparative Evaluation of Two Formulation Approaches for Dabigatran Etexilate Mesylate The two formulation approaches for dabigatran etexilate mesylate as shown below were evaluated:

(i) First approach being that of the present invention having two types of particles/pellets (one of dabigatran etexilate mesylate and the other of organic acid) and (ii) Second approach having one type of particles/pellets having both dabigatran etexilate mesylate and organic acid. This formulation was prepared according to the teachings of WO 03/074056 and, in particular, Example 1. Formulation (B)

(A) Preparation of formulation A having two types of particles/pellets (i.e. Dabigatran etexilate mesylate granules and seal coated tartaric acid pellets)

TABLE 17

Composition of Dabigatran etexilate mesylate granules

| Ingredients | mg/capsule |
|---|---|
| Intragranular | |
| Dabigatran etexilate mesylate equivalent to 150 mg dabigatran etexilate | 172.95 |
| IPA | q.s |
| Extragranular | |
| Microcrystalline cellulose | 67.05 |
| Croscarmellose Sodium | 50 |
| Total weight of the Dabigatran etexilate mesylate granules | 290 |

TABLE 18

| Composition of seal coated tartaric acid pellets | |
| --- | --- |
| Ingredients | mg/capsule |
| Tartaric acid (TAP ® 600) | 196.34 |
| Seal coating of Tartaric acid pellets | |
| Hydroxypropylmethyl cellulose | 5.62 |
| Lactose | 5.62 |
| Talc | 8.42 |
| Isopropyl alcohol-water | q.s |
| Total weight of seal coated pellets | 216 |

Procedure:

(i) Preparation of Dabigatran Etexilate Mesylate Granules Portion

Loaded weighed quantity of dabigatran etexilate mesylate in the granulator and granulated it using isopropyl alcohol. The granules were further dried in fluidized bed drier. The granules were then sized, sifted and blended with microcrystalline cellulose, croscarmellose sodium in a suitable blender to give dabigatran etexilate mesylate granules portion.

(ii) Preparation of Seal Coated Tartaric Acid Pellets

Hydroxypropyl cellulose was added to a suitable quantity of isopropyl alcohol water mixture under continuous stirring to obtain a clear solution. Lactose was added to this solution and mixed, followed by addition of talc and stirring. The suspension thus formed was filtered through a suitable sieve and sprayed under continuous stirring on tartaric acid pellets using a fluidized bed coater with Wurster column to achieve desired weight gain. The coated tartaric acid pellets were then dried.

The lubricated seal coated tartaric acid pellets and dabigatran etexilate mesylate granules were filled in capsules using the automatic capsule filling machine in HPMC size 0 capsules.

(C) Comparative evaluation of dissolution profiles of formulation of the present invention having two types of particles/pellets (Formulation A above) and formulation having one type of particles/pellets (Formulation B above)

Dissolution profiles of the formulations in 0.01N HCl pH 2 media at 100 rpm USP type I (basket) are as depicted under A and B below:

| | % release | |
| --- | --- | --- |
| Time (minutes) | Formulation A (two types of particles/pellets) | Formulation B (one type of particles/pellets) |
| 10 | 65.1 | 19.2 |
| 15 | 79.2 | 57 |
| 20 | 86.7 | 86.1 |
| 30 | 92 | 97 |
| 45 | 95.5 | 97.6 |
| 60 | 96.8 | 98.5 |

Comparative evaluation of dissolution profiles of formulation of the present invention having two types of particles/pellets (Formulation A above) and formulation having one type of particles/pellets (Formulation B above) indicates that formulations of the present invention having two types of particles/pellets can provide faster dissolution particularly at earlier time points as compared to formulation having one type of particles/pellets. Such a faster dissolution at earlier time points can ensure availability of more amount of active especially when (a) absorption of the active is rapid with faster Tmax (~45 minutes-1 hour), (b) significant bioactivation is involved and (c) negligible and variable absorption at higher pH.

The invention claimed is:

1. A composition comprising: a mixture of at least two distinct types of particles wherein
    a) the first type of particles comprise dabigatran etexilate in the form of the free base or in the form of a pharmaceutically acceptable salt or polymorph thereof, wherein the first type of particles is free from organic acids and inorganic acids; and
    b) the second type of particles comprise at least one pharmaceutically acceptable organic acid, wherein the second type of particles is coated with a protective coating layer and is free from dabigatran etexilate.

2. The composition according to claim 1, further comprising at least one pharmaceutically acceptable excipient.

3. The composition according to claim 1, comprising from 0.01 wt % to 90 wt % of dabigatran etexilate, as dabigatran etexilate mesylate.

4. The composition according to claim 1, comprising from 2 wt % to 95 wt % of the at least one pharmaceutically acceptable organic acid.

5. A unit dosage form prepared from the composition according to claim 1, which comprises from 50 mg to 200 mg of dabigatran etexilate mesylate.

6. A process for the preparation of the composition according to claim 2, comprising the step of mixing the first type of particles and the second type of particles with the at least one pharmaceutically acceptable excipient.

7. The process of claim 6, wherein the first type of particles are prepared by granulation.

8. The process according to claim 7, comprising the steps of:
    i) blending dabigatran etexilate in the form of the free base or in the form of a pharmaceutically acceptable salt or polymorph thereof and at least one pharmaceutically acceptable excipient;
    ii) granulating the blend of step (i) with a binder solution to form granules of dabigatran etexilate;
    iii) blending at least one organic acid and at least one pharmaceutically acceptable excipient;
    iv) granulating the blend of step (iii) with a binder solution to form organic acid granules;
    v) coating the organic acid granules with a protective coating layer;
    vi) blending the granules of step (ii) with the coated granules of step (v) to form a mixture of at least two types of granules;
    vii) optionally blending the mixture of at least two types of granules of step (vi) with at least one pharmaceutically acceptable excipient;
    viii) adding a lubricant to the blend of step (vii);
    ix) filling the lubricated mixture of step (viii) into suitable hard capsules.

9. The process according to claim 7, comprising the steps of:
    i) blending dabigatran etexilate in the form of the free base or in the form of a pharmaceutically acceptable salt or polymorph thereof and at least one pharmaceutically acceptable excipient;
    ii) granulating the blend of step (i) with a binder solution to form granules of the dabigatran etexilate;

iii) blending at least one organic acid and at least one pharmaceutically acceptable excipient;
iv) extruding and spheronizing the blend of step (iii) to form organic acid pellets;
v) coating the organic acid pellets of step (iv) with a protective coating layer;
vi) blending the granules of step (ii) with the coated pellets of step (v) to form a mixture of at least two types of particles;
vii) optionally blending the mixture of at least two types of granules of step (vi) with at least one pharmaceutically acceptable excipient;
viii) adding a lubricant to the blend of step (vii);
ix) filling the lubricated mixture of step (viii) into suitable hard capsules.

10. The composition according to claim 2, wherein the at least one pharmaceutically acceptable excipient is selected from the group consisting of binders, disintegrants, diluents, surfactants, glidants, lubricants, and combinations thereof.

11. A composition consisting of a mixture of two distinct types of particles and at least one pharmaceutically acceptable excipient, wherein
   a) the first type of particles comprise dabigatran etexilate in the form of the free base or in the form of a pharmaceutically acceptable salt or polymorph thereof, wherein the first type of particles is free from organic and inorganic acids; and
   b) the second type of particles comprise at least one pharmaceutically acceptable organic acid, wherein the second type of particles is coated with a protective coating layer and is free from dabigatran etexilate.

12. The composition according to claim 11, comprising from 0.01 wt % to 90 wt % of dabigatran etexilate, as dabigatran etexilate mesylate.

13. The composition according to claim 11, wherein the first type of particles comprise at least one pharmaceutically acceptable excipient.

14. The composition according to claim 11, wherein the at least one pharmaceutically acceptable excipient is selected from the group consisting of binders, disintegrants, diluents, surfactants, glidants, lubricants, and combinations thereof.

15. A capsule unit dosage form prepared from the composition according to claim 14, which comprises from 50 mg to 200 mg of dabigatran etexilate mesylate.

16. A capsule containing a pharmaceutical composition consisting of a mixture of two distinct types of particles and at least one pharmaceutically acceptable excipient, wherein
   a) the first type of particles comprise dabigatran etexilate in the form of the free base or in the form of a pharmaceutically acceptable salt or polymorph thereof, wherein the first type of particles is free from organic and inorganic acids; and
   b) the second type of particles comprise at least one pharmaceutically acceptable organic acid, wherein the second type of particles is coated with a protective coating layer and is free from dabigatran etexilate.

17. The capsule according to claim 16 containing from 50 mg to 200 mg of dabigatran etexilate mesylate.

18. The capsule according to claim 16, wherein the first type of particles comprise at least one pharmaceutically acceptable excipient.

* * * * *